United States Patent [19]

Isaacs et al.

[11] Patent Number: 4,820,858
[45] Date of Patent: Apr. 11, 1989

[54] PROCESS FOR THE PREPARATION OF 2-(HYDROXYALKYL)ACRYLIC COMPOUNDS

[75] Inventors: Neil S. Isaacs, Henley-on-Thames; Jonathan Hill, Reading, both of England

[73] Assignee: Stamicarbon B.V., Geleen, Netherlands

[21] Appl. No.: 169,137

[22] Filed: Mar. 18, 1988

Related U.S. Application Data

[63] Continuation of Ser. No. 841,838, Mar. 20, 1986, abandoned.

[30] Foreign Application Priority Data

Mar. 20, 1985 [NL] Netherlands .......................... 8500804

[51] Int. Cl.$^4$ .................. C07C 121/30; C07C 121/34; C07C 121/48; C07C 121/70
[52] U.S. Cl. ....................................... 558/372; 549/59; 549/60; 549/75; 549/78; 549/472; 549/473; 549/491; 549/497; 558/371; 560/60; 560/183; 568/433; 568/459; 568/312; 568/388; 564/170; 564/201
[58] Field of Search .................. 558/371, 372; 560/60, 560/183; 568/433, 459, 312, 388; 564/170, 201

[56] References Cited

U.S. PATENT DOCUMENTS 3,743,669 7/1973 Hillman et al. ...................... 558/371

Primary Examiner—Joseph Paul Brust
Attorney, Agent, or Firm—Cushman, Darby & Cushman

[57] ABSTRACT

The invention relates to a process for the preparation of 2-(hydroxyalkyl)acrylic compounds having the formula

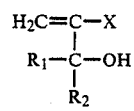

wherein X represents a —CN group, a —COOR$_3$ group, a —COR$_4$ group or a —CONR$_4$R$_5$ group wherein R$_3$ is an alkyl group containing 1–4 C atoms and R$_4$ and R$_5$ independently represent an H atom or R$_3$, and wherein R$_1$ and R$_2$ independently represent an H atom or an alkyl group with 1–4 C atoms or an (hetero) aryl group, or R$_1$ and R$_2$ together represent a cyclic compound with 5–12 C atoms by contacting an acrylic compound H$_2$C=CH—X with a carbonyl compound of the formula

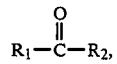

wherein X, R$_1$ and R$_2$ denote the same as in the above, this being effected in the liquid phase in the presence of a tertiary amine, characterized in that the reaction is carried out at a pressure in excess of 500 bar in excess of 500 bar, advantageously 1,500–18,000 bar.

7 Claims, No Drawings

PROCESS FOR THE PREPARATION OF 2-(HYDROXYALKYL)ACRYLIC COMPOUNDS

This is a continuation of application Ser. No. 06/841,838 filed Mar. 20, 1986, which is abandoned.

The invention relates to a process for the preparation of 2-(hydroxyalkyl)acrylic compounds having the formula

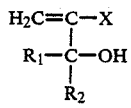

wherein X represents a —CN group, a —COOR$_3$ group, a —COR$_4$ group or a —CONR$_4$R$_5$ group wherein R$_3$ is an alkyl group containing 1-4 C atoms and R$_4$ and R$_5$ independently represent an H atom or R$_3$, and
wherein R$_1$ and R$_2$ independently represent an H atom or an alkyl group with 1-4 C atoms or an (hetero) aryl group or R$_1$ and R$_2$ together represent a cyclic compound with 5-12 C atoms
by contacting an acrylic compound H$_2$C=CH—X with a carbonyl compound of the formula

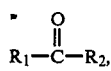

wherein X, R$_1$ and R$_2$ denote the same as in the above, this being effected in the liquid phase in the presence of a tertiary amine.

Such a process for the coupling of carbonyl compounds with acrylic compounds is described in U.S. Pat. No. 3,743,669. According to this state of the art, the desired 2-(hydroxyalkyl)acrylic compounds can be obtained, on the basis of the examples performed batchwise, in yields of between 59 and 76%, calculated as the product of conversion and selectivity. An important drawback of the process according to U.S. Pat. No. 3,743,669 is the extremely long reaction time, which may vary from many hours to many days. Another drawback is that only aldehydes can be used as carbonyl compounds, so that the field of compounds which can be prepared is rather limited. In Example IV of U.S. Pat. No. 3,743,669 methyl ethyl ketone is even used as an inert solvent.

The object of this invention is to eliminate these drawbacks. The invention therefore provides a process for the preparation of 2-(hydroxyalkyl)acrylic compounds having the formula

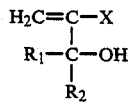

wherein X represents a —CN group, a —COOR$_3$ group, a —COR$_4$ group or a —CONR$_4$R$_5$ group wherein R$_3$ is an alkyl group containing 1-4 C atoms and R$_4$ and R$_5$ independently represent an H atom or R$_3$, and
wherein R$_1$ and R$_2$ independently represent an H atom or an alkyl group with 1-4 C atoms, or an (hetero) aryl group, or R$_1$ and R$_2$ together represent a cyclic compound with 5-12 C atoms
by contacting an acrylic compound H$_2$C=CH—X with a carbonyl compound of the formula

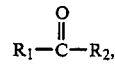

wherein X, R$_1$ and R$_2$ denote the same as in the above, this being effected in the liquid phase in the presence of a tertiary amine, characterized in that the reaction is carried out at a pressure in excess of 500 bar.

Examples of (hetero) aryl groups are defined above are eventually substituted phenyl, naphthyl, furyl and thienyl. Substituents may be for instance alkyl groups with 1-4 C-atoms, chlorine, bromine, iodine and phenyl, but other substituents are not excluded from the scope of the invention provided the substituents are inert under the reaction conditions.

The process according to the invention enables preparation of the desired acrylic compounds in a relatively short time, ranging from, for instance, less than one minute to a few hours, depending on the reactants. Moreover the process according to the invention may be effected with ketones as carbonyl groups containing starting material as well as with aldehydes.

Acrylic compounds obtained in the process according to the present invention may be used as monomers in resin-type products and possess good adhesive properties.

Suitable acrylic starting compounds are, for instance, acrylonitrile, methyl acrylate, ethyl acrylate, acrolein, methyl vinyl ketone and acrylamide.

As ketone or aldehyde use can be made of, for instance, formaldehyde, acetaldehyde, benzaldehyde, 4-phenylbenzaldehyde, acetone, methyl ethyl ketone and cyclohexanone.

The catalyst is a tertiary amine, applied in an amount of up to 20 wt.%, calculated upon the quantity of ketone or aldehyde. Catalysts that may for instance be applied are trialkyl amines with e.g. 1-4 C-atoms per alkyl group, e.g. dimethyl ethyl amine (NMe$_2$Et) and diethyl methyl amine (NMeEt$_2$) or, if a catalyst having a higher activity is desirable, diazabicyclo-[2,2,2]-octane (DABCO).

In the process according to the invention optionally an inert organic solvent can be applied, depending on the desired reaction. Examples of suitable solvents are ethers e.g. tetrahydrofuran (THF) and diethylether. The reaction generally is somewhat slower in the presence of a solvent. Solvents may therefore be of advantage in reactions that would proceed too fast and would yield carbonized final products if no solvent were applied.

The pressure at which the liquid-phase reaction can be applied generally exceeds 500 bar and more in particular in between 1500 and 18,000 bar. The required pressure will be determined experimentally, depending on the starting materials used. For economic reasons, naturally, it is desirable to choose a pressure in this high-pressure range that is as low as possible. Although the reactions according to the invention also proceed at a pressure above 18,000 bar, these very high pressures offer no additional advantages over the above-mentioned range.

The process according to the invention can generally be applied at room temperature, but when using some less reactive starting materials it may be desirable to apply a higher temperature, for instance up to 100° C. or higher.

The molar ratio of the reactants will generally be 1:1, but other ratios are also possible, e.g. between 1:10 to 10:1.

Summarizing, many embodiments are possible within the purview of the invention, which comprises the preparation of 2-(hydroxyalkyl) acrylic compounds in the liquid phase at a high pressure. For each reaction the optimal conditions, such as catalyst choice, catalyst concentration, amounts of the reactants, presence or absence of a solvent, pressure applied, reaction time and temperature applied, can be established by some preliminary experiments.

The invention will be elucidated in the following examples, without being restricted thereto.

Example I

A high-pressure vessel was charged with 60 mmoles acrylonitrile, 60 mmoles acetaldehyde, 4 ml THF and 5 mmoles $NMe_2Et$. The vessel was closed and the pressure of the liquid reaction mixture was increased to 12,000 bar, the temperature being 20° C. Within 1 minute after reaching the final pressure, the yield of 2-(1-hydroxyethyl)acrylonitrile (according to gas-liquid chromatography), calculated as the product of conversion and selectivity relative to acrylonitrile, was 96.2%.

Comparative Example A

In the same way as described in Example I, the reaction was performed under autogeneous pressure at 150° C. After 6 hours reaction time, the yield of 2-(1-hydroxyethyl)acrylonitrile was 3.8%.

Example II

The same vessel as described in Example I was charged with 60 mmoles acrylonitrile, 60 mmoles of formaldehyde, 4 ml THF and 0.5 mmoles DABCO. After 1 hour reaction time at 20° C. and 5000 bar the yield of 2-(hydroxymethyl)acrylonitrile amounted to 85%.

Example III

Example I was repeated, without THF being added and at 5000 bar. The 2-(1-hydroxyethyl)acrylonitrile yield after 5 minutes was 78%.

Example IV

The same vessel as described in Example I was charged with 60 mmoles acrylonitrile, 60 mmoles acetaldehyde and 1.2 mmoles DABCO. After 5 hours reaction at 35° C. and 5000 bar the yield of 2-(1-hydroxyethyl)acrylonitrile was 98%.

Comparative Example B

Example IV was repeated with a pressure of 1 bar. After 5 hours the yield of 2-(1-hydroxyethyl)acrylonitrile was 10%.

Example V

Example III was repeated with 60 mmoles propanal instead of the acetaldehyde. After 5 minutes the 2-(1-hydroxypropyl)acrylonitrile yield was 57%.

Example VI

Example III was repeated with 60 mmoles benzaldehyde instead of the acetaldehyde, 2.5 mmoles DABCO being used as a catalyst. After 5 minutes a 2-(1-hydroxy-1-phenylmethyl)acrylonitrile yield of 98% was reached.

Example VII

Example I was repeated, using 60 mmoles acetone instead of acetaldehyde. After an hour the 2-(2-hydroxypropyl)acrylonitrile yield was 92%.

Example VIII

The same vessel as described in Example I was charged with 60 mmoles methyl ethyl ketone, 60 mmoles acrylonitrile and 1.2 mmoles DABCO. After 5 hours reaction time at 20° C. and 5000 bar the yield of 2-(2-hydroxybutyl)acrylonitrile was 87%.

Example IX

Example III was repeated with 60 mmoles acetone instead of the acetaldehyde, 2.5 mmoles DABCO being used as catalyst. After a reaction time of 5 minutes at 35° C. the 2-(2-hydroxypropyl)acrylonitrile yield was 98%.

Example X

Example III was repeated with 60 mmoles cyclohexanone instead of the acetaldehyde, 2.5 mmoles DABCO being used as catalyst. After 18 hours reacting, 50% of the cyclohexanone was found to have been converted. The yield of 2-(1-hydroxycyclohexyl)acrylonitrile was 41%.

Example XI

Example I was repeated with 60 mmoles ethyl acrylate instead of acrylonitrile. After 10 minutes reacting at 20° C., the 2-(1-hydroxyethyl)-ethylacrylate yield was found to be 98%.

Example XII

The same vessel as described in Example I was charged with 60 mmoles acetaldehyde, 60 mmoles acrylamide and 5 mmoles $NMe_2Et$. After 3 hours reaction time at 20° C. and 5000 bar the yield of 2-(1-hydroxyethyl)acrylamide was 83%.

Example XIII

The same vessel as described in Example I was charged with 60 mmoles acrylonitrile, 60 mmoles 4-phenylbenzaldehyde and 1.2 mmoles DABCO. After 2 hours reaction time at 20° C. and 5000 bar the yield of 2-[hydroxy(4-phenyl)phenylmethyl]acrylonitrile was 86%.

Example XIV

The same vessel as described in Example I was charged with 60 mmoles acrolein, 60 mmoles acetaldehyde and 5% by weight $NMeEt_2$. After 25 minutes reaction time at 20° C. and 15000 bar, the yield of 2-(1-hydroxyethyl)acrolein was 95%.

Example XV

Example XIV was repeated with 60 mmoles proprionaldehyde instead of acetaldehyde under further identical conditions. The yield of 2-(1-hydroxypropyl)acrolein was 95%.

Example XVI

The vessel described in Example I was charged with 60 mmoles methyl vinyl ketone, 60 mmoles acetaldehyde and 1.2 mmoles DABCO. After 30 minutes reaction time at 20° C. and 5000 bar the yield 2-(1-hydroxyethyl)methyl vinyl ketone was 83%.

We claim:

1. Process for the preparation of 2-(hydroxyalkyl)acrylic compounds having the formula

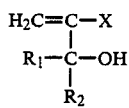

wherein X represents a —CN group, a —COOR$_3$ group, a —COR$_4$ group or a —CONR$_4$R$_5$ group wherein R$_3$ is an alkyl group containing 1–4 C atoms and R$_4$ and R$_5$ independently represent an H atom or R$_3$, and wherein R$_1$ and R$_2$ and independently represent an H atom or an alkyl group with 1–4 C atoms or a (hetero) aryl selected from the group consisting of phenyl, naphthyl, furyl and thienyl, or R$_1$ and R$_2$ together represent a carbocyclic compound with 5–12 C atoms by contacting an acrylic compound H$_2$C=CH—X with a carbonyl compound of the formula

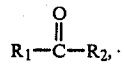

wherein X, R$_1$ and R$_2$ denote the same as in the above, this being effected in the liquid phase in the presence of a, tertiary amine selected from the group consisting of trialkylamines with 1–4 C-atoms per alkyl group and diazabicyclo-(2,2,2)-octane as a catalyst, the reaction being carried out at a pressure between 5,000 and 18,000 bar.

2. Process according to claim 1, characterized in that as starting carbonyl compound use is made of formaldehyde, acetaldehyde, propanal, benzaldehyde, 4-phenylbenzaldehyde, acetone, methyl ethyl ketone or cyclohexanone.

3. Process according to claim 1, characterized in that as acrylic starting compound use is made of acrylonitrile, methyl acrylate, ethyl acrylate, acrolein, methyl vinyl ketone or acrylamide.

4. Process according to claim 1, characterized in that as catalyst use is made of dimethyl ethyl amine, diethyl methyl amine or diazabicyclo[2,2,2]-octane.

5. Process according to claim 1, characterized in that the reaction is carried out in the presence of an inert organic solvent.

6. Process according to claim 5, characterized in that as inert organic solvent use is made of tetrahydrofuran or diethylether.

7. Process according to claim 1, characterized in that the reaction is carried out at a temperature between 20° and 100° C.

* * * * *